US009476956B2

(12) United States Patent
Taniguchi et al.

(10) Patent No.: US 9,476,956 B2
(45) Date of Patent: Oct. 25, 2016

(54) MAGNETIC RESONANCE IMAGING APPARATUS WITH CORRECTION OF MAGNETIC FIELD GRADIENT WAVEFORM DISTORTION

(75) Inventors: Yo Taniguchi, Tokyo (JP); Suguru Yokosawa, Tokyo (JP); Yoshitaka Bito, Tokyo (JP)

(73) Assignee: HITACHI, LTD., Tokyo (JP)

( * ) Notice: Subject to any disclaimer, the term of this patent is extended or adjusted under 35 U.S.C. 154(b) by 636 days.

(21) Appl. No.: 13/984,537

(22) PCT Filed: Jan. 19, 2012

(86) PCT No.: PCT/JP2012/051089
§ 371 (c)(1),
(2), (4) Date: Aug. 9, 2013

(87) PCT Pub. No.: WO2012/124375
PCT Pub. Date: Sep. 20, 2012

(65) Prior Publication Data
US 2013/0314090 A1 Nov. 28, 2013

(30) Foreign Application Priority Data
Mar. 16, 2011 (JP) ................................. 2011-057952

(51) Int. Cl.
*G01R 33/56* (2006.01)
*A61B 5/055* (2006.01)
(Continued)

(52) U.S. Cl.
CPC ............... *G01R 33/56* (2013.01); *A61B 5/055* (2013.01); *G01R 33/56554* (2013.01); *G01R 33/56572* (2013.01); *G01R 33/5614* (2013.01); *G01R 33/5616* (2013.01)

(58) Field of Classification Search
CPC ............ G01R 33/56; G01R 33/56554; G01R 33/56572; G01R 33/5614; G01R 33/5616; A61B 5/055
See application file for complete search history.

(56) References Cited

U.S. PATENT DOCUMENTS 4,752,735 A 6/1988 Onodera et al.
5,270,654 A * 12/1993 Feinberg ............ G01R 33/5615
324/307

(Continued)

FOREIGN PATENT DOCUMENTS

JP 62-152443 7/1987
JP 10-33501 2/1998
JP 2001-78986 3/2001

OTHER PUBLICATIONS

Notification of Transmittal of Translation of the IPRP—PCT/JP2012/051089, dated Oct. 10, 2013 (form PCT/IB/338) [1 pg.).

(Continued)

Primary Examiner — G. M. Hyder
(74) Attorney, Agent, or Firm — Baker Botts L.L.P.

(57) ABSTRACT

In order to improve image quality, a technique for obtaining information for eliminating distortions of the k-space in the readout direction and the phase encoding direction caused by the waveform distortion of the gradient magnetic field pulse is provided. A pulse sequence for the main scan is used to repeatedly measure echoes with changing the time integral value of the dephasing pulse for the readout gradient magnetic field. In the above measurement, the phase encoding pulse is not made zero, but two-dimensional data are measured in the same manner as that of the main scan. By using the measured two-dimensional data, correction information for eliminating distortions of the k-space in the readout direction and the phase encoding direction caused by the waveform distortion of the gradient magnetic field pulse is calculated in each of the readout direction and the phase encoding direction.

15 Claims, 13 Drawing Sheets

(51) Int. Cl.
*G01R 33/565* (2006.01)
*G01R 33/561* (2006.01)

(56) References Cited

U.S. PATENT DOCUMENTS

| | | | |
|---|---|---|---|
| RE35,656 E * | 11/1997 | Feinberg | G01R 33/5615 324/307 |
| 5,914,601 A | 6/1999 | Goldfarb | |
| 6,362,621 B1 | 3/2002 | Miyamoto et al. | |
| 2011/0112393 A1 * | 5/2011 | Taniguchi | A61B 5/055 600/410 |

OTHER PUBLICATIONS

International Preliminary Report on Patentability—PCT/JP2012/051089, Oct. 1, 2013 (form PCT/IB/373) [1 pg.].

Written Opinion of the International Searching Authority (translation)—PCT/JP2012/051089, Mar. 19, 2012 (form PCT/ISA/237) [3 pgs.].

* cited by examiner

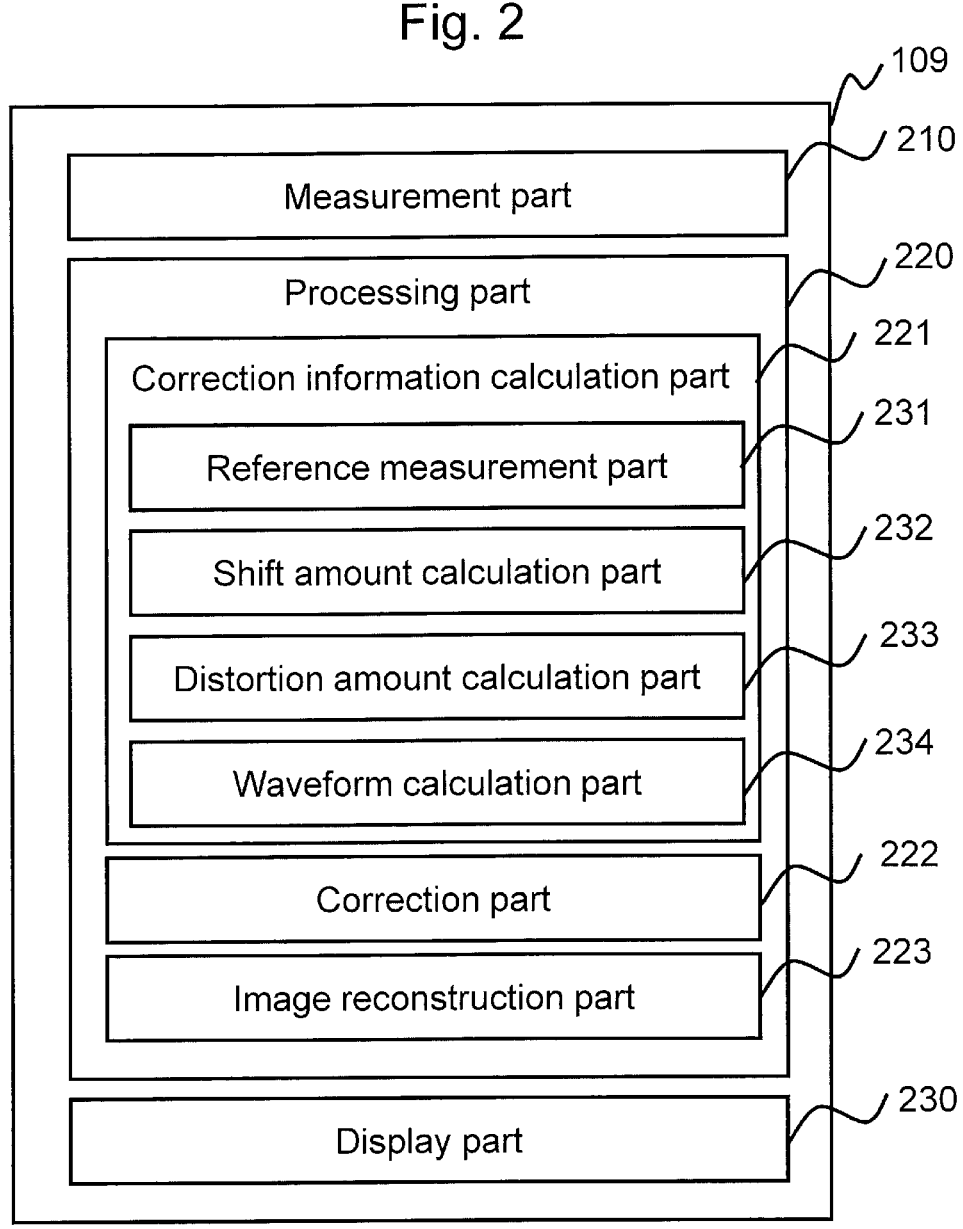

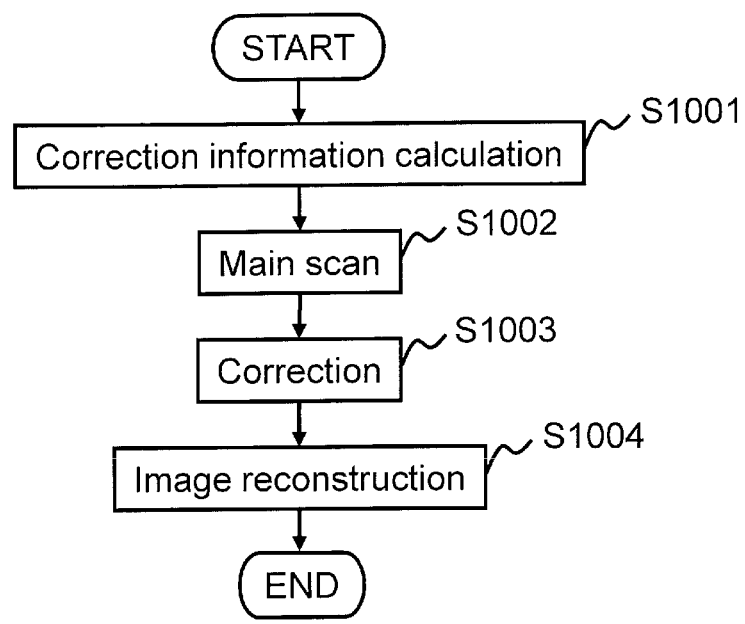

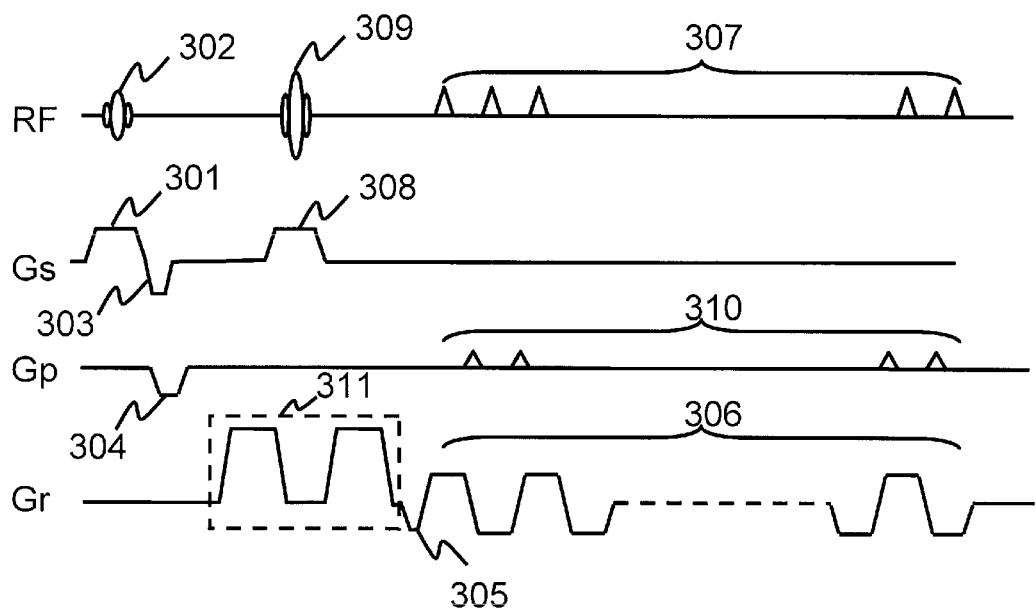
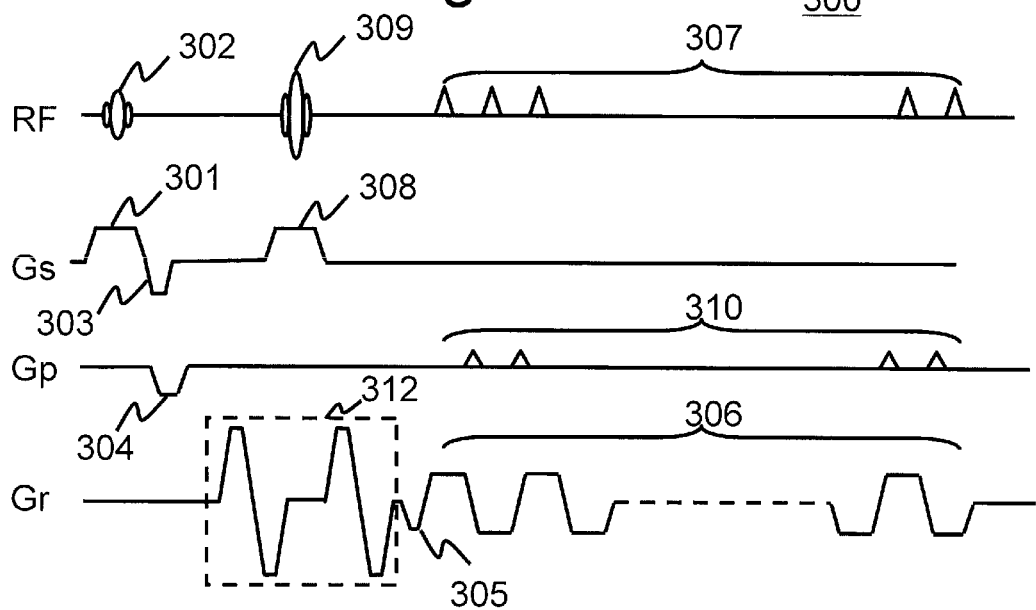

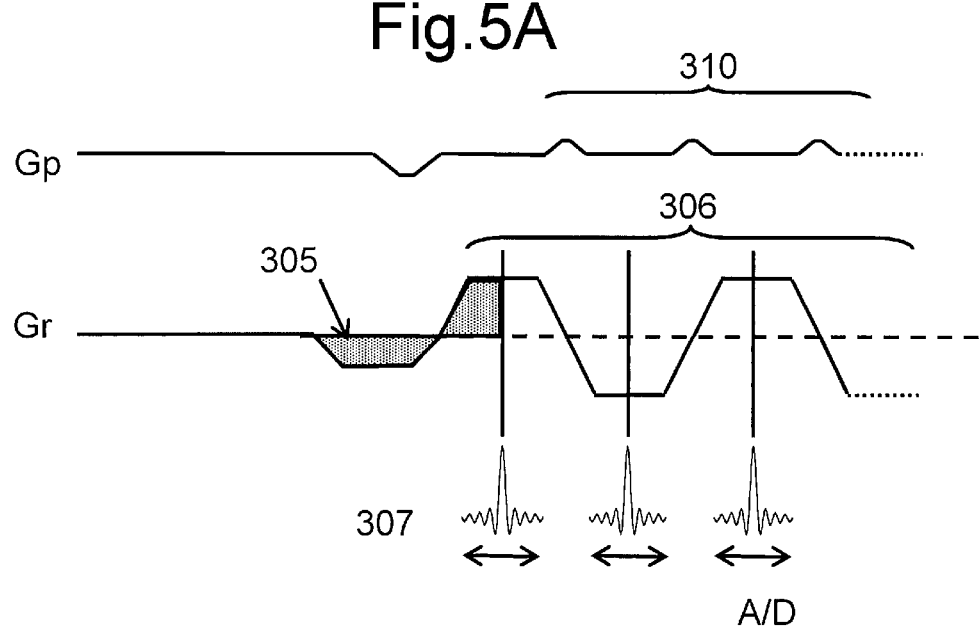
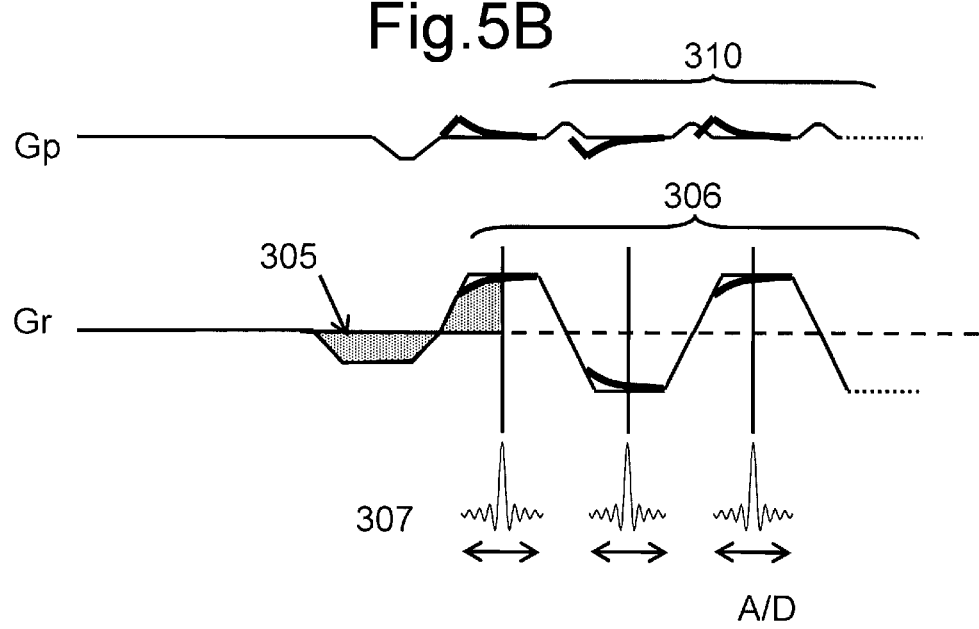

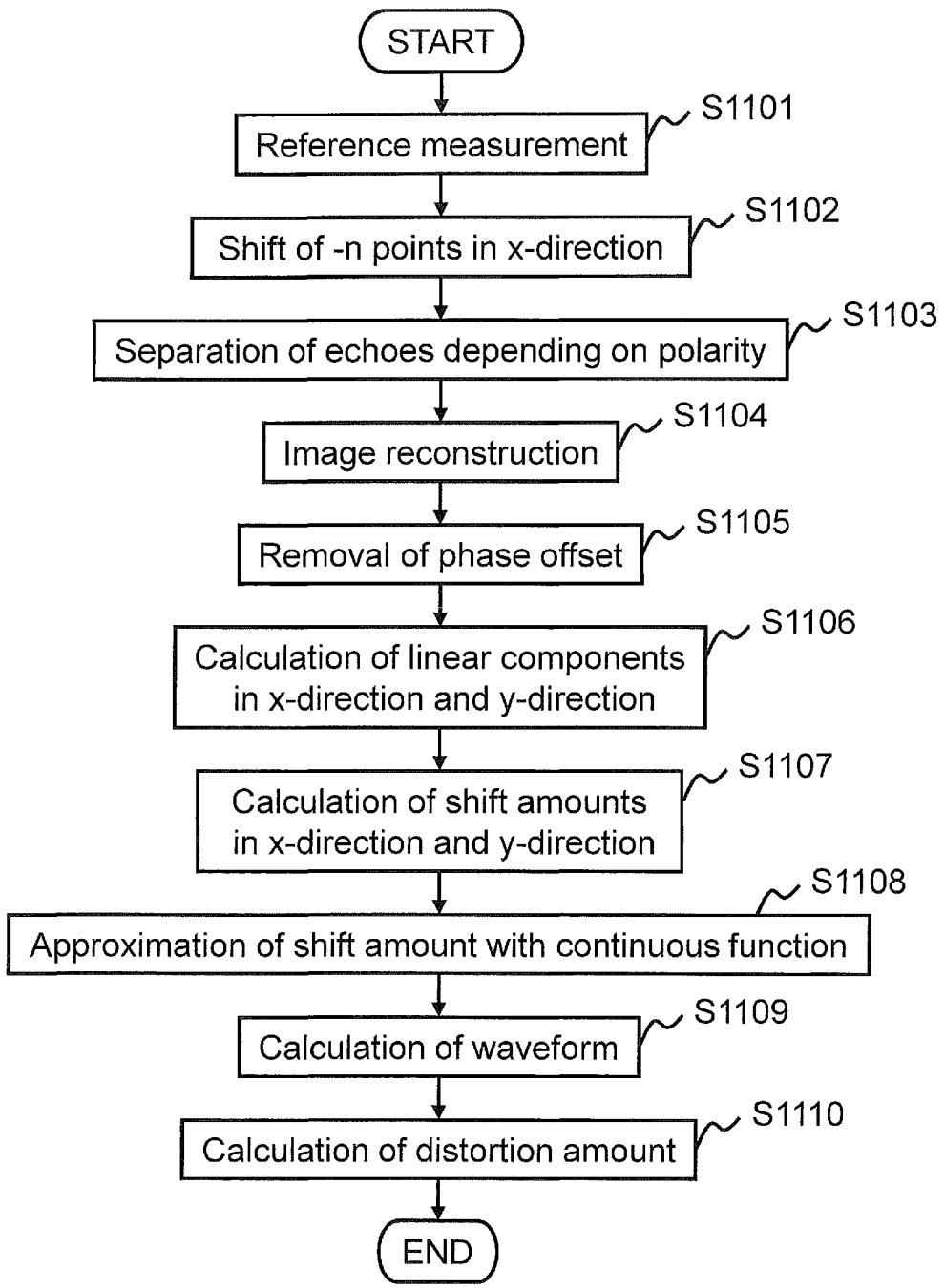

Fig.13A
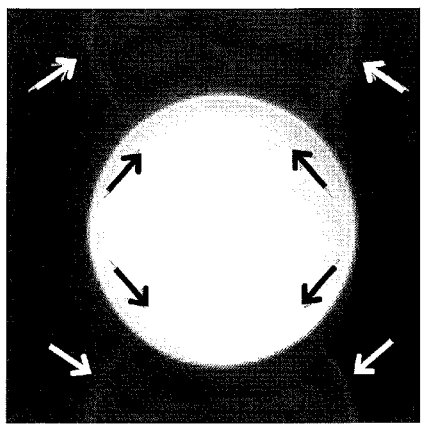 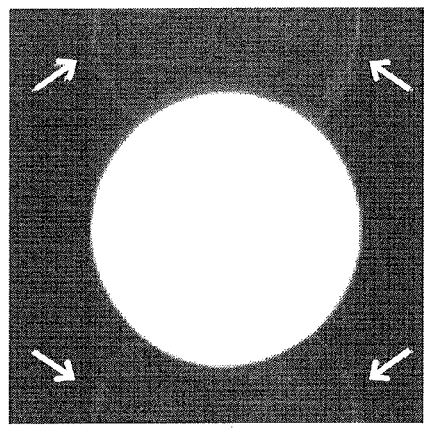
510         511
Fig.13B
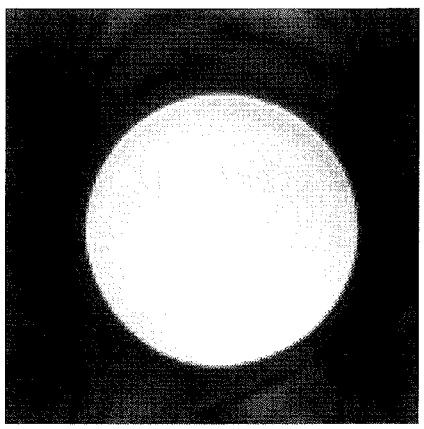 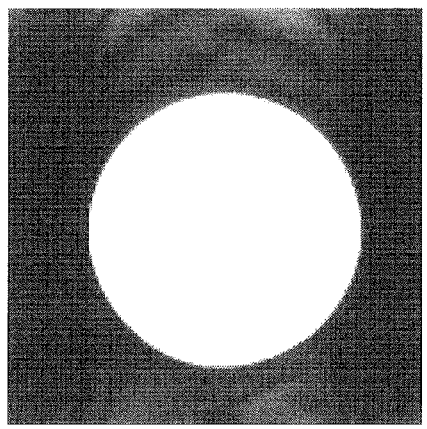
520         521

MAGNETIC RESONANCE IMAGING APPARATUS WITH CORRECTION OF MAGNETIC FIELD GRADIENT WAVEFORM DISTORTION

TECHNICAL FIELD

The present invention relates to a magnetic resonance imaging (MRI) technique. In particular, the present invention relates to such a technique for correcting influence of waveform distortion of a gradient magnetic field applied in order to give positional information.

BACKGROUND ART

Magnetic resonance imaging (MRI) apparatuses are medical diagnostic imaging apparatuses with which a radio frequency magnetic field and a gradient magnetic field are applied to a subject placed in a static magnetic field, and signals generated from the subject by the nuclear magnetic resonance are measured and used to construct images. In the MRI apparatuses, in general, a slice gradient magnetic field for determining a section to be imaged (imaging section) and an excitation pulse for exciting magnetization in the imaging section are simultaneously applied, and nuclear magnetic resonance signals (echoes) generated when the excited magnetization converges are obtained. The measured echoes are arranged in the k-space defined with a horizontal axis kx and a vertical axis ky, subjected to inverse Fourier transform, and thereby reconstructed into an image.

At the time of the echo measurement, in order to give positional information to the magnetization, a phase encoding gradient magnetic field pulse and a readout gradient magnetic field pulse are applied in perpendicular directions in the imaging plane. In order to give accurate positional information, application times and intensities of both the gradient magnetic field pulses must be accurately controlled.

The radio frequency magnetic field pulse for generating echoes and the gradient magnetic field pulse are applied in accordance with an imaging sequence set beforehand. As this imaging sequence, various kinds of sequences are known for various purposes. High-speed imaging methods enabling imaging in a short time include EPI (echo-planar imaging), BASG (balanced steady-state acquisition with rewound gradient echo), and so forth.

EPI is a method of realizing high-speed measurement by repeatedly applying a readout gradient magnetic field pulse with reversing the polarity thereof at a cycle of about 2 ms to continuously generate echoes. BASG is a method of realizing high-speed measurement by repeating excitation of magnetization and measurement of echo at a cycle of several milliseconds.

In such high-speed imaging methods, a phase encoding pulse is applied in a short time, and then echo is measured during or immediately after rise of the readout gradient magnetic field pulse in order to shorten the imaging time. For the design of the pulse sequence, the readout gradient magnetic field pulse is assumed to have a rectangular shape, and an image is reconstructed from the echoes arranged in the k-space on the basis of the above assumption.

However, waveform of the readout gradient magnetic field pulse is actually distorted during or immediately after the rise of the pulse. This is caused by output characteristics of a gradient magnetic field amplifier itself, inductance of a gradient coil, eddy current induced by application of the gradient magnetic field pulse, and so forth. With such distortion of the waveform of the readout gradient magnetic field pulse, arrangement positions of the echoes in the k-space shifts from the intended positions, and so-called distortion of the k-space is thereby generated to generate artifacts such as distortion and ghost in reconstructed images.

As a technique for avoiding this distortion of the k-space, there is a method of measuring waveform of the readout gradient magnetic field pulse, calculating distortion of the k-space in the readout direction from the obtained waveform, and correcting the distortion (refer to, for example, Patent document 1). Specifically, in EPI, echoes are repeatedly measured with making the phase encoding gradient magnetic field pulse zero and changing time integral value of the dephase pulse of the readout gradient magnetic field. Further, on the basis of time shift amounts of the individual echoes, shapes of individual readout gradient magnetic field pulses are calculated, and distortion of the k-space in the readout direction is calculated. By correcting the calculated distortion, an image is reconstructed with suppressing artifacts generated by the distortion of waveform of the readout gradient magnetic field pulse.

PRIOR ART REFERENCES

Patent Document

Patent document 1: Japanese Patent Unexamined Publication (Kokai) No. 62-152443

DISCLOSURE OF INVENTION

Problem to be Solved by the Invention

However, the eddy current generated by the readout gradient magnetic field pulse is actually generated not only in the application direction of the gradient magnetic field, but also in the direction perpendicular to the application direction. Therefore, distortion of the k-space is also generated not only in the readout direction, but also in the phase encoding direction. Moreover, eddy current is generated also by the phase encoding gradient magnetic field, although amplitude thereof is small because amplitude of the pulse is small. By the method described in Patent document 1, distortion of the k-space caused by the eddy current generated in the readout direction can be corrected. However, information on distortion of the k-space induced by the eddy current generated in the phase encoding direction cannot be obtained, and therefore this distortion cannot be eliminated.

The present invention was accomplished in light of the aforementioned circumstances, and an object of the present invention is to provide a technique for obtaining information for eliminating distortions of the k-space in the readout direction and the phase encoding direction caused by the waveform distortion of the gradient magnetic field pulse, in order to improve image quality.

Means to Solve the Problem

According to the present invention, a pulse sequence for the main scan is used to repeatedly measure echoes with changing the time integral value of the dephasing pulse for the readout gradient magnetic field. In this measurement, the phase encoding pulse is not made zero, but two-dimensional data are measured in the same manner as that of the main scan. By using the measured two-dimensional data, correction information for eliminating distortions of the k-space in the readout direction and the phase encoding direction caused by the waveform distortion of the gradient magnetic field pulse is calculated for each of the readout direction and the phase encoding direction.

Specifically, the present invention provides a magnetic resonance imaging apparatus comprising a signal measurement part for applying a radio frequency magnetic field and a gradient magnetic field to a subject placed in a static magnetic field and measuring magnetic resonance signals generated from the subject, and a processor for controlling the signal measurement part and processing the magnetic resonance signals measured by the signal measurement part, wherein the processor comprises a correction information calculator for calculating correction information used for eliminating distortion of the measured magnetic resonance signals, and the correction information calculator comprises a reference measurement part for controlling the signal measurement part to repeat a unit measurement consisting of applying a readout gradient magnetic field and a phase encoding gradient magnetic field with changing phase encoding amount to repeatedly obtain echoes, and arranging a plurality of the obtained echoes in the k-space to obtain one set of k-space data with changing dephase readout amount to obtain a plurality of sets of k-space data, and a shift amount calculator for calculating shift amounts of peak positions of the echoes in the application direction of the readout gradient magnetic field and the application direction of the phase encoding gradient magnetic field from the plurality of sets of the k-space data, and calculates the correction information by using the calculated shift amounts.

Effect of the Invention

According to the present invention, information for eliminating distortions of the k-space in the readout direction and the phase encoding direction caused by the waveform distortion of the gradient magnetic field pulse can be obtained for the purpose of improving image quality.

BRIEF DESCRIPTION OF DRAWINGS

FIG. 2 is a functional block diagram of a computer according to an embodiment of the present invention.

FIG. 3 is a flowchart of measurement processing according to the present invention.

FIG. 4A shows a sequence for DWEPI according to an embodiment of the present invention, which uses standard MPG pulses.

FIG. 4B shows a sequence for DWEPI according to an embodiment of the present invention, which uses bipolar type MPG pulses.

FIG. 5A is an explanatory drawing for explaining the relationship between the gradient magnetic field pulse and echo for a case where the readout pulse has an ideal shape.

FIG. 5B is an explanatory drawing for explaining the relationship between the gradient magnetic field pulse and echo for a case where the readout pulse shape is distorted.

FIG. 7 is a flowchart of the correction information calculation processing according to an embodiment of the present invention.

FIG. 13A is an explanatory drawing for explaining an image reconstructed from the k-space data shown in FIG. 12 without correction.

FIG. 13B is an explanatory drawing for explaining an image reconstructed from the k-space data shown in FIG. 12 after correction of the k-space data according to an embodiment of the present invention.

MODES FOR CARRYING OUT THE INVENTION

Hereafter, embodiments of the present invention will be explained. In all the drawings for explaining the embodiments of the present invention, elements having the same function are indicated with the same numerals, and repetitive explanations thereof are omitted.

Figure 1:
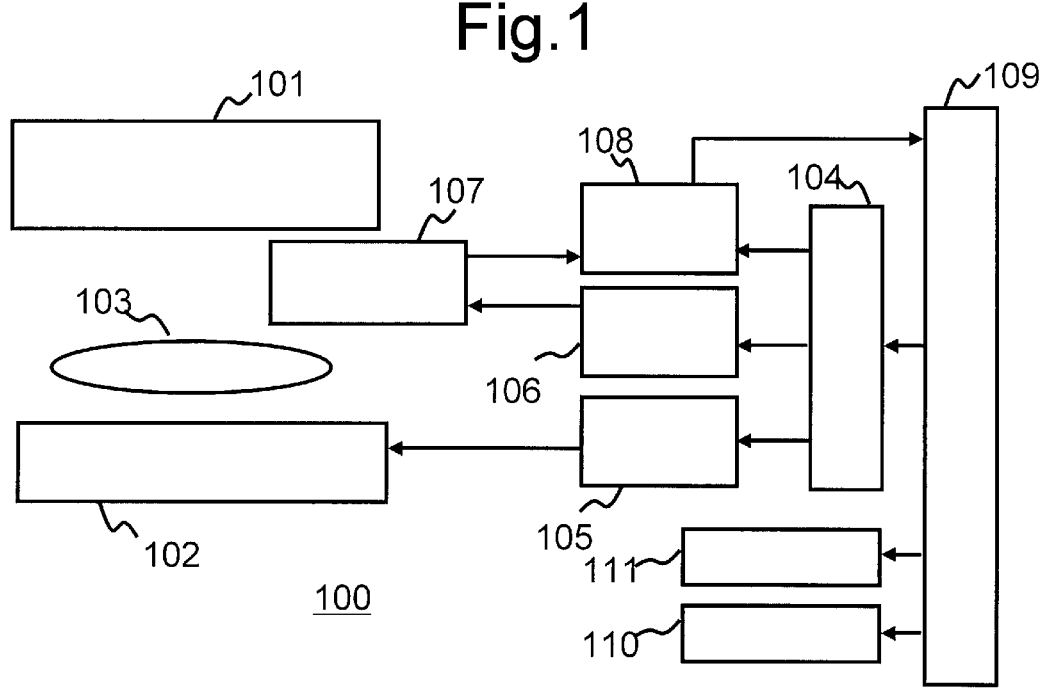
FIG. 1 is a block diagram showing general configuration of an MRI apparatus according to an embodiment of the present invention.

First, an MRI apparatus according to an embodiment of the present invention will be explained. FIG. 1 is a block diagram showing a general configuration of MRI apparatus 100 according to this embodiment. The MRI apparatus 100 is provided with a magnet 101 for generating a static magnetic field, a gradient coil 102 for generating a gradient magnetic field, a sequencer 104, a gradient magnetic field power supply 105, a radio frequency magnetic field generator 106, a probe 107 for irradiating a radio frequency magnetic field and detecting a magnetic resonance signal (echo), a receiver 108, a computer 109, a display 110, and a storage medium 111. A subject 103 (for example, living body) is placed on a bed (table) or the like, and is placed in a static magnetic field space generated by the magnet 101.

The sequencer 104 sends commands to the gradient magnetic field power supply 105 and the radio frequency magnetic field generator 106 to make them generate a gradient magnetic field and a radio frequency magnetic field, respectively. The generated radio frequency magnetic field is irradiated on the subject 103 via the probe 107. Echoes generated from the subject 103 are received by the probe 107, and detected by the receiver 108. Nuclear magnetic resonance frequency as the basis of detection (detection reference frequency $f_0$) is set by the sequencer 104. The detected signals are sent to the computer 109, and signal processing such as image reconstruction is performed by the computer. The results are displayed on a display 110. The detected signals and measurement conditions may be stored in the storage medium 111, as required.

The sequencer 104 operates the parts at timings and intensities programmed beforehand. Directions for the operations are sent from the computer 109. Among programs, a program describing timings and intensities of the radio frequency magnetic field, gradient magnetic field, and signal reception is peculiarly called a pulse sequence. Various pulse sequences suitable for various purposes are known. The MRI apparatus 100 of this embodiment uses such a pulse sequences as those for EPI, DWEPI, and BASG, which enable detection of echoes in a short time.

The computer 109 of this embodiment operates the parts of the MRI apparatus 100, measures echoes according to a pulse sequence, and obtains an image of a desired contrast from the measured echoes. In order to realize this image acquisition, the computer 109 of this embodiment is provided with, as shown in FIG. 2, a measurement part 210 for sending directions to the sequencer 104 according to the pulse sequence to measure echoes, and arranging them in the k-space, a processing part 220 for controlling the measurement by the measurement part 210 and processing the echoes arranged in the k-space, and an display part 230 for displaying results of the processing performed by the processing part 220 on the display 110.

According to this embodiment, in the processing part 220, amounts of distortion of the measured echoes resulting from the waveform distortion of the gradient magnetic field pulse are corrected. For realizing this correction, the processing part 220 is provided with a correction information calculation part 221 for calculating correction information for correcting the echoes, a correction part 222 for correcting the echoes by using the correction information, and an image reconstruction part 223 for reconstructing an image from the corrected echoes.

The correction information is information used for eliminating distortion of the magnetic resonance signals, and the correction information calculation part 221 of this embodiment calculates shift amounts of echo peaks in both the readout direction and the phase encoding direction, distortion amount of the k-space, and waveform of the readout gradient magnetic field pulse as correction information. For realizing this calculation, the correction information calculation part 221 of this embodiment is provided with a reference measurement part 231, a shift amount calculation part 232, a distortion amount calculation part 233, and a waveform calculation part 234.

The reference measurement part 231 performs reference measurement for obtaining echoes used for calculation of the correction information for correction of distortion resulting from the waveform distortion of the gradient magnetic field pulse. According to this embodiment, the same imaging sequence as that for the echo measurement for image reconstruction (henceforth referred to as main scan) is repeatedly executed with changing only application amount of the dephase gradient magnetic field pulse applied in the readout direction and without changing the other conditions to obtain a plurality of k-space data. That is, the phase encoding gradient magnetic field pulse is not made zero, but it is executed in the main scan. Therefore, the obtained k-space data becomes two-dimensional k-space data from which one image can be reconstructed. In addition, the reference measurement part 231 sends directions to the measurement part 210 to perform reference measurement.

The shift amount calculation part 232 calculates shift amounts of echo peaks caused by distortion of the readout gradient magnetic field by using a plurality of the k-space data obtained by the reference measurement. The shift amount calculation part 232 calculates shift amount hr in the readout direction and shift amount hp in the phase encoding direction as the shift amounts. In addition, the shift amount of echo peak is calculated for every application amount of the dephase gradient magnetic field pulse.

The distortion amount calculation part 233 calculates amount of distortion of the k-space from the shift amount hr in the readout direction and the shift amount hp in the phase encoding direction calculated by the shift amount calculation part 232. The distortion amount calculation part 233 calculates a point kr in the readout direction actually sampled for a sampling point m on the k-space, and shift Δkp(m) in the phase encoding direction as the distortion amount.

The waveform calculation part 234 calculates pulse waveform of a readout pulse 306 from the shift amount hr for the readout direction and the shift amount hp in the phase encoding direction calculated by the shift amount calculation part 232. As the pulse waveform, time change Gr(m) of gradient magnetic field amplitude Gr of the readout gradient magnetic field pulse for each sampling point is calculated by differentiating the shift amounts hr and hp.

The correction part 222 performs gridding processing of the echoes measured in the main scan on the basis of the distortion amount calculated by the distortion amount calculation part 233 to calculate values on the grid of the k-space.

The image reconstruction part 223 reconstructs an image by using the values on the grid after the correction.

These functions of the computer 109 are realized by CPU of the computer 109 by loading programs stored in the storage medium 111 to a memory, and executing them.

The flow of the measurement according to this embodiment performed by these parts will be explained. As shown in the flowchart of FIG. 3, the correction information calculation part 221 first performs the correction information calculation processing (Step S1001). Then, the measurement part 210 performs the main scan (Step S1002), the correction part 222 corrects results (k-space data) of the main scan by using the correction information (Step S1003), and the image reconstruction part 223 reconstructs an image by using the corrected k-space data (Step S1004).

The correction information calculation processing is performed by using the same pulse sequence as that for the main scan. Therefore, if the pulse sequences used for a plurality of the main scans are the same, it is not necessary to perform the correction information calculation processing for every main scan.

The details of the correction information calculation processing performed by the correction information calculation part 221 in Step S1001 will be explained below by exemplifying a case of using a DWEPI sequence used for one of the EPI methods as a pulse sequence for the main scan. In advance of explanation of the correction information calculation processing, the DWEPI sequence will be explained first.

FIGS. 4A and 4B shows the DWEPI sequences 300. In these figures, RF, Gs, Gp, and Gr represent axes of the radio frequency magnetic field, slice gradient magnetic field, phase encoding gradient magnetic field, and readout gradient magnetic field, respectively. This embodiment will be explained below by exemplifying an example in which the slice direction along which the aforementioned slice gradient magnetic field pulse Gs is applied to determine a slice position is defied as the z-direction, the readout direction along which the readout gradient magnetic field pulse Gr is applied is defined as the x-direction, and the phase encoding direction along which the phase encoding gradient magnetic field pulse Gp is applied is defined as the y-direction.

As shown in FIGS. 4A and 4B, with the DWEPI sequence 300, a radio frequency magnetic field (RF) pulse 302 of the proton resonance frequency $f_h$ is first irradiated together with application of a slice gradient magnetic field pulse 301 in the z-direction to excite protons in the predetermined slice of the subject 103. Then, after a slice rephase gradient magnetic field pulse 303 and a phase encoding gradient magnetic field pulse 304 for dephase for giving positional information in the phase encoding direction (y-direction) to magnetization are applied, a 180-degree pulse 309 is irradiated with application of a slice gradient magnetic field pulse 308 in the z-direction. Further, MPG pulses 311 (312) are applied before and after the 180-degree pulse 309. In this example, they are applied, for example, in the readout direction (x-direction).

Then, with applying a readout gradient magnetic field pulse 305 for dephase (dephase pulse), and an alternately positive/negative readout gradient magnetic field pulse (readout pulse) 306 in order to give positional information in the readout direction, a plurality of magnetic resonance signals (echoes) 307 are measured. At the time of this measurement, in order to give positional information in the phase encoding direction, whenever the echo 307 is measured, a blipped phase encoding gradient magnetic field pulse (phase encoding pulse) 310 is applied.

The MPG pulse 311 (312) may be applied in any of the slice direction, the readout direction, and the phase encoding direction. As the shape of the MPG pulse 311 (312), there are the standard MPG pulse 311 applied in only one of the positive and negative directions shown in FIG. 4A, and the bipolar type MPG pulse 312 shown in FIG. 4B, and it may be any of these. Since the bipolar type MPG pulse 312 is a combination of positive and negative pulses, it can more suppress the generation of eddy current compared with the standard MPG pulse 311.

Although the DWEPI sequence is exemplified among the pulse sequences for the EPI methods, the pulse sequence is not limited to this sequence. Since distortion of the k-space caused by the readout gradient magnetic field pulse is corrected in this embodiment, the pulse sequence to be executed may be a usual EPI sequence with which the MPG pulse 311 (312) is not applied. Further, when the DWEPI sequence is used, it is preferable to make the MPG pulse zero. Diffusion emphasis is thereby cancelled, signals of higher SN ratios are thereby obtained, and therefore accuracy of the distortion calculation is improved. Further, in the case of an apparatus suffering from large eddy current components of a long time constant, artifacts are generated in images by eddy currents induced by MPG, and therefore it is also preferable to make the amplitude of MPG zero, or use a usual EPI sequence.

Hereafter, the correction information calculation processing performed by the correction information calculation part 221 for the case of using the aforementioned DWEPI sequence for the main scan will be explained with an example of the measurement. First, distortion of the k-space caused by distortion of the readout pulse 306 (and phase encoding pulse 310) will be explained.

Timing charts of the phase encoding pulse 310, the readout pulse 306, and the sampling (A/D) of echo 307 after the dephase pulse 305 in the Gr direction in the DWEPI sequences 300 shown in FIGS. 4A and 4B are shown in FIG. 5A. As explained above, after the application of the dephase pulse 305, one echo 307 is measured whenever the readout pulse 306 is inverted.

During each sampling (A/D), when the time integration of the magnetic field gradient in the Gr direction becomes 0, amplitude of the echo 307 is maximized (echo peak). Therefore, if it is assumed that the time integral value of the dephase pulse 305 (application amount) is ½ of the application amount of each readout pulse 306 applied during the sampling (A/D), the position of the echo peak should be the center of each A/D, in an ideal case where the waveform of the readout pulse 306 is a correctly trapezoidal shape as shown in FIG. 5A.

Figure 6A:
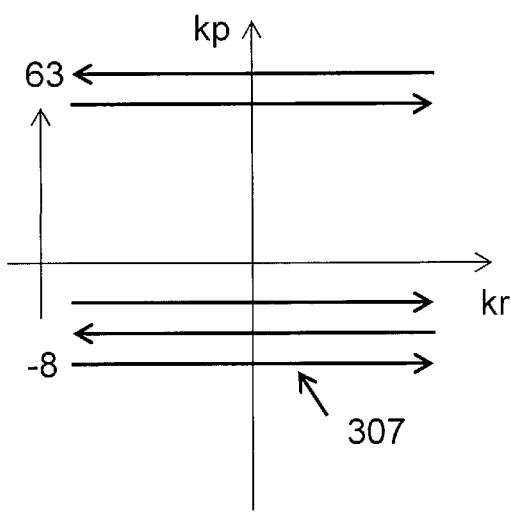
FIG. 6A is an explanatory drawing for explaining the k-space arrangement for a case where the readout pulse has an ideal shape.

Here, the measured echoes 307 are arranged along the readout direction (kr) on the k-space, as shown in FIG. 6A. In this case, the sampling rate for A/D is fixed, and sampling point number is 256 for double field of view. Further, the phase encoding amount given with the phase encoding pulse 310 is from −8 to +63, and 72 echoes are measured. The image reconstruction part 223 reconstructs an image of 256×128 pixels from these k-space data by using the half Fourier method, and then cuts both ends of the field of view in the readout direction to finally reconstruct an image of 128×128 pixels.

However, in an actual measurement, the MRI apparatus 100 suffers from waveform distortion of the readout pulse 306 itself, and eddy currents generated by both the gradient magnetic field pulses of the readout pulse 306 and the phase encoding pulse 310, and therefore the waveforms of the readout pulse 306 and the phase encoding pulse 310 are distorted. This phenomenon is schematically shown in FIG. 5B with thick lines.

Figure 6B:
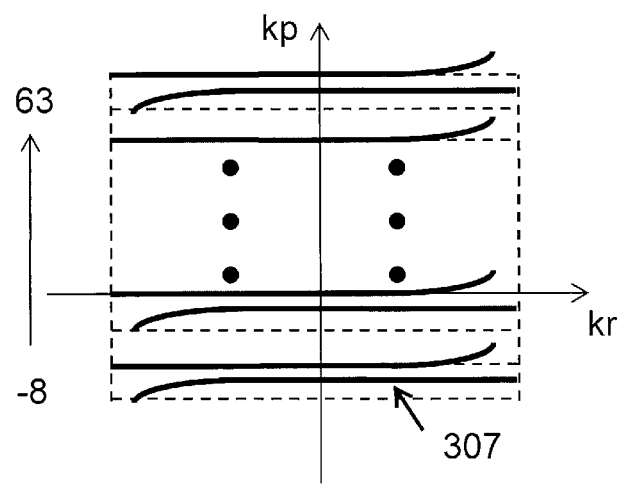
FIG. 6B is an explanatory drawing for explaining the k-space arrangement for a case where the readout pulse shape is distorted.

Arrangement of the echoes 307 on the k-space in this case is shown in FIG. 6B. As shown in this drawing, the echoes 307 are not linearly arranged on the k-space in this case as shown in FIG. 6A, but are arranged along distorted lines. As shown in this drawing, the k-space is distorted in the kr direction in a degree corresponding to the distortion of the readout gradient magnetic field and the distortion caused by eddy current, and the blip amount is changed and distorted in the kp direction in a degree corresponding to the distortion of the phase encoding pulse 310 and the distortion caused by eddy current. If an image is reconstructed with an assumption that the echoes 307 are arranged as shown in FIG. 6A without taking the distortions into consideration, artifacts and distortion are generated in the image.

The correction information calculation part 221 of this embodiment obtains correction information that enables determination of the k-space distortion shown in FIG. 6B by the correction information calculation processing. The flow of the correction information calculation processing will be explained with reference to FIG. 7. The correction information calculation processing is started with a direction given by an operator.

First, the reference measurement part 231 performs reference measurement for calculation of correction information (Step S1101). The reference measurement part 231 repeatedly executes the DWEPI sequence 300 used for the main scan with changing only the application amount of the dephase pulse 305 as the reference measurement. A plurality of two-dimensional k-space data are thereby obtained. The measurement for obtaining echoes that enable reconstruction of one image is henceforth referred to as unit measurement.

Figure 8:
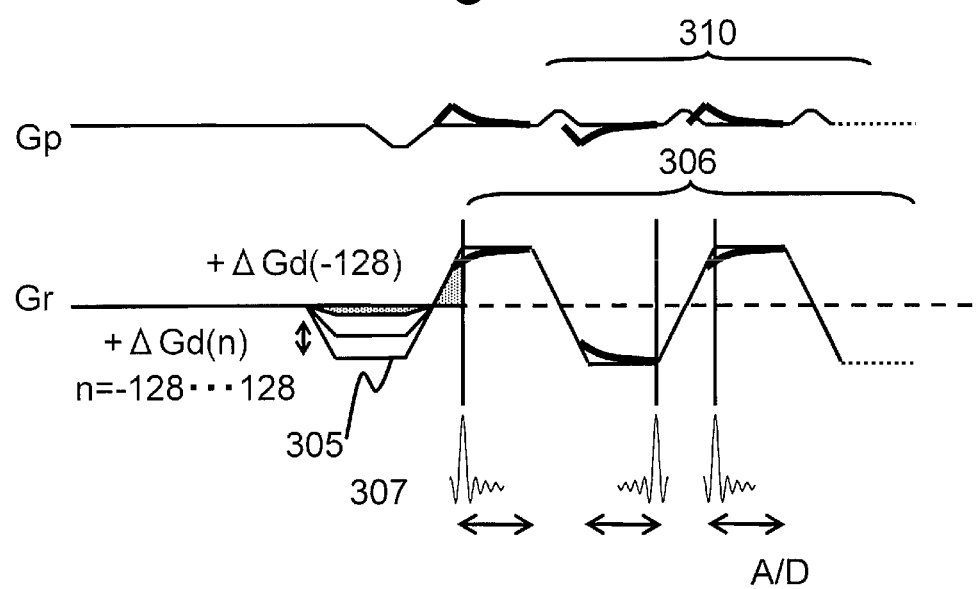
FIG. 8 is an explanatory drawing for explaining the pulse sequence of the reference measurement according to an embodiment of the present invention.

The application amount of the dephase pulse 305 is changed for every unit measurement so that, when the amplitude of the readout pulse 306 during A/D is fixed to be a value equal to the set amplitude, the peak of echo 307 (echo peak) moves by a predetermined number of sampling points, as shown in FIG. 8. If the application amount is changed by a constant amount for every unit measurement, the following processings such as function fitting become easier. The range within which the application amount of the dephase pulse 305 is changed is, for example, from 0 to ½ of the application amount of the readout pulse 306. Further, the application amount can be changed by changing the application time and amplitude of the gradient magnetic field. However, when change of the application time may provides overlap of the dephase pulse with the readout pulse 306, amplitude is changed. If amplitude of the readout pulse 306 is represented as Gr, sampling interval is represented as Δts, and echo peak moves by n of sample points, change amount ΔGd(n) of time integral value (application amount) Gd(n) of the dephase pulse 305 to be applied is represented by the following equation (1).

$$\Delta Gd(n) = nGr\Delta ts \ (n=-128, \ldots, 128) \quad (1)$$

The application amount of the dephase pulse 305 before the change thereof is represented as Gd(0). The reference measurement part 231 of this embodiment repeats application of the dephase pulse 305 at an application amount represented by the equation (2), and execution of the DWEPI sequence with changing n. The position of the echo peak is thereby shifted forward and backward for every unit measurement, and a plurality of different two-dimensional k-space data are obtained.

$$Gd(n) = Gd(0) + \Delta Gd(n) \ (n=-128, \ldots, 128) \quad (2)$$

In addition, increment of n can be determined to be an arbitrary value according to size of the waveform distortion. That is, when the waveform distortion is large, the increment of n is made small (for example, 1) to measure precisely. On the other hand, when the waveform distortion is small, the increment of n is made large. If the increment is made large, total number of data to be obtained can be made small, and therefore the measurement time can be shortened. However, the measurement is necessarily performed for the case where n is 0. In the following example of the measurement, the increment of n is 4, and 65 of data are measured.

Then, the shift amount calculation part 232 performs the shift amount calculation processing. In this processing, each of the obtained k-space data are first shifted by −n of points in the readout direction (x-direction) (Step S1102).

When the amplitude of the readout pulse 306 during A/D is equal to the set amplitude Gr and fixed, the shift amount of the echo peak is proportional to the application amount of the dephase pulse 305. Therefore, whenever the application amount of the dephase pulse 305 is changed, the echo peak shifts by n of sample points. For example, when n is −128, and the readout pulse 306 is a trapezoid wave as set, the echo peak of each echo 307 shifts by 128 sample points, and locates at the end of A/D, as shown in FIG. 8.

However, when the amplitude of the readout pulse 306 is not constant due to eddy current or power supply characteristics, the shift amount of the echo peak is not proportional to the change of the application amount of the dephase pulse 305. The shift amount calculation part 232 of this embodiment estimates amplitude change of the readout pulse 306 from deviation amount of the shift amount of the echo peak from that value observed when the shift amount is proportional to the application amount of the dephase pulse 305. That is, if it is found that the waveform of the readout pulse 306 is not distorted in the processing of Step S1101, the echo peak of each data is determined to be the origin. On the other hand, when the waveform contains distortion, the echo peak is determined to locate at a position shifted from the origin according to the distortion.

Then, the shift amount calculation part 232 divides the echoes of each shifted k-space data set s(n) into two groups according to the sign (polarity) of the readout pulse 306 (Step S1103). Each k-space data measured with a positive readout pulse 306 is represented as $s_+(n)$, and each k-space data measured with a negative readout pulse 306 is represented as $s_-(n)$.

Figure 9A:
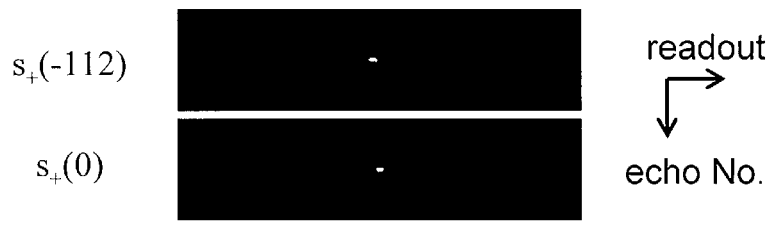
FIG. 9A is an explanatory drawing for explaining shifted k-space data according to an embodiment of the present invention.

As an example of the measurement, actually obtained k-space data $s_+(-112)$ and $s_+(0)$ are shown in FIG. 9A. By observing the echo peaks (bright spots) of them, it can be seen that $s_+(-112)$ locates slightly left from $s_+(0)$. This indicates that the echo peak shifts to the left more greatly than the shift amount corresponding to decrease of the dephase amount. From the above, it can be seen that the amplitude of the readout pulse 306 is slightly smaller than the set value. As for the major imaging conditions for the example of the measurement, field of view was 250 mm, TR/TE was $1000/65$ ms, the slice thickness was 10 mm, the matrix size was 128×128, the echo number was 72, and the echo interval was 1 ms.

Then, the shift amount calculation part 232 reconstructs images from $s_+(n)$ and $s_-(n)$ by the half Fourier transform (Step S1104). The reconstructed images are referred to as $I_+(n)$ and $I_-(n)$, respectively. When the echo peaks of $s_+(n)$ and $s_-(n)$ deviate from the origin, the phase of each image has a liner inclination.

Figure 9B:
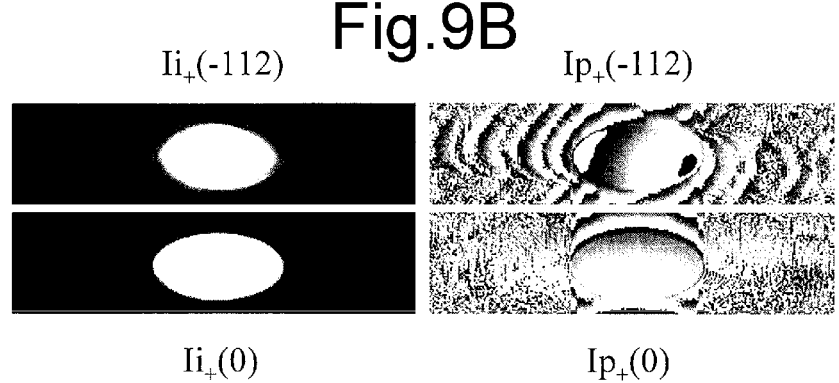
FIG. 9B is an explanatory drawing for explaining an intensity image and a phase image reconstructed from the k-space data shown in FIG. 9A.

Intensity images $Ii_+(-112)$ and $Ii_+(0)$ as well as phase images $Ip_+(-112)$ and $Ip_+(0)$ reconstructed from $s_+(-112)$ and $s_+(0)$ shown in FIG. 9A are shown in FIG. 9B. As shown in $Ip_{30}(-112)$, it can be seen that the phase of $I_+(-112)$ significantly inclines along the readout direction (x-direction). Further, as shown in $Ip_+(0)$, the phase of $I_+(0)$ scarcely inclines along the x-direction, but slightly inclines along the phase encoding direction (y-direction) (phase offset).

Then, the shift amount calculation part 232 creates a phase image in which the phase offset is cancelled (Step S1105). In this step, the phase offset is cancelled by dividing the obtained $I_+(n)$ and $I_-(n)$ with $I_+(0)$ and $I_-(0)$, respectively. That is, $I_+(n)/I_+(0)$ and $I_-(n)/I_-(0)$ are calculated.

Figure 9C:
FIG. 9C is an explanatory drawing for explaining a phase image obtained from the phase image shown in FIG. 9B after offset removal.
Figure 9D:
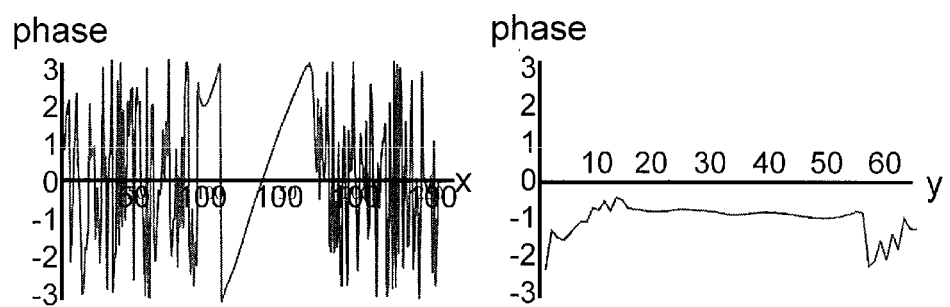
FIG. 9D is an explanatory drawing for explaining a phase graph obtained from the phase image shown in FIG. 9B after offset removal.

A phase image obtained after cancellation of the phase offset $(I_+(-112)/I_+(0))$ is shown in FIG. 9C. Further, graphs of phase change in the x- and y-directions are shown in FIG. 9D. Two of the graphs shown in FIG. 9D show phases on straight lines in the x-direction and y-direction passing through the center of the image, respectively. It can be seen that a significant inclination is observed in the x-direction, but almost no inclination is observed in the y-direction. That is, it can be said that influence of the cross-talk of the readout pulse 306 is smaller compared with that of the waveform distortion of the readout pulse 306 in this case.

Then, the shift amount calculation part 232 calculates a linear component er of the phase change (phase change along the straight line in the x-direction passing through the center of the image (origin)) in the readout direction (x-direction) and a linear component ep of the phase change (phase change along the straight line in the y-direction passing through the origin) in the phase encoding direction (y-direction) for each phase image obtained after the cancellation of the offset (phase images of $I_+(n)/I_+(0)$ and $I_-(n)/I_-(0)$) (Step S1106).

Then, the shift amount calculation part 232 calculates a shift amount hr of the echo peak in the readout direction (x-direction) and a shift amount hp of the echo peak in the phase encoding direction (y-direction) by using the obtained linear components er and ep according to the following equations (3) and (4), respectively (Step S1107).

$$hr(n)=256er(n)/(2\pi) \quad (3)$$

$$hp(n)=128ep(n)/(2\pi) \quad (4)$$

Then, the shift amount calculation part 232 determines a continuous function hcr(n) and a continuous function hcp(n) by function fitting from the echo peak shift amount hr(n) in the x-direction and the echo peak shift amount hp(n) in the y-direction, respectively (Step S1108). The shift amount calculation part 232 of this embodiment outputs the shift amounts hr(n) and hcr(n) in the readout direction, as well as the shift amounts hp(n) and hcp(n) in the phase encoding direction as shift amounts. The shift amounts hr(n) and hcr(n) in the readout direction, as well as the shift amounts hp(n) and hcp(n) in the phase encoding direction are independently calculated from k-space data obtained with the positive polarity and k-space data obtained with the negative polarity, respectively.

For example, as the fitting function hcr(n) and hcp(n) for hr(n) and hp(n), $a+b\cdot\exp(c\cdot n)+d\cdot n$ is used. Further, when linear component of n is not observed, it may be $a+b\cdot\exp(c\cdot n)$. In this example of the measurement, a linear component was observed in the readout direction and linear component was not observed in the phase encoding direction, and therefore $hcr(n)=a+b\cdot\exp(c\cdot n)+d\cdot n$ and $hcp(n)=a+b\cdot\exp(c\cdot n)$ are used.

The shift amounts determined by the shift amount calculation part 232 of this embodiment from the example of the measurement shown in FIG. 9 are shown in FIG. 10. FIG. 10A shows the shift amount in the readout direction calculated from the k-space data obtained with the readout pulse 306 of positive polarity, FIG. 10B shows the shift amount in the readout direction calculated from the k-space data obtained with the readout pulse 306 of negative polarity, FIG. 10C shows the shift amount in the phase encoding direction calculated from the k-space data obtained with the readout pulse 306 of positive polarity, and FIG. 10D shows the shift amount in the phase encoding direction calculated from the k-space data obtained with the readout pulse 306 of negative polarity. Further, in these graphs, the vertical axes indicate shift amounts, the horizontal axes indicate n, dots represent the calculated shift amounts hr and hp, and the solid lines indicate values of the calculated fitting functions her and hcp.

Figure 10A:
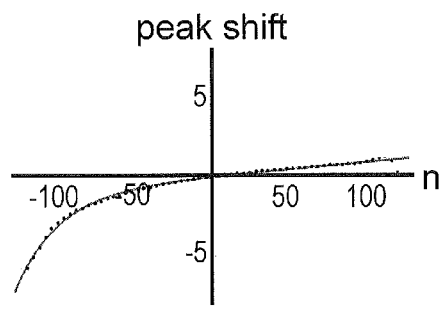
FIG. 10A is a graph of calculated peak shift amounts according to an embodiment of the present invention.
Figure 10B:
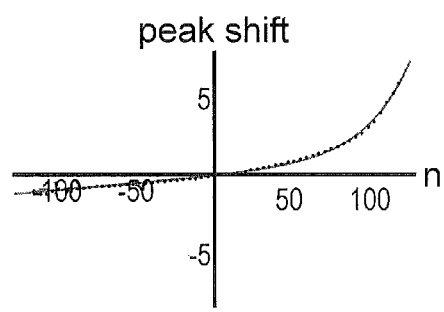
FIG. 10B is a graph of calculated peak shift amounts according to an embodiment of the present invention.
Figure 10C:
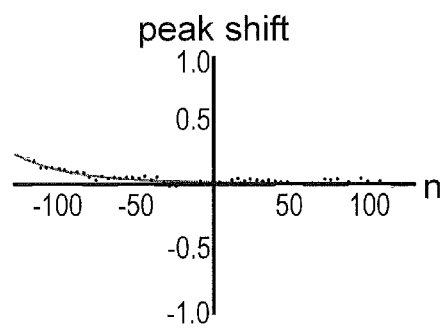
FIG. 10C is a graph of calculated peak shift amounts according to an embodiment of the present invention.
Figure 10D:
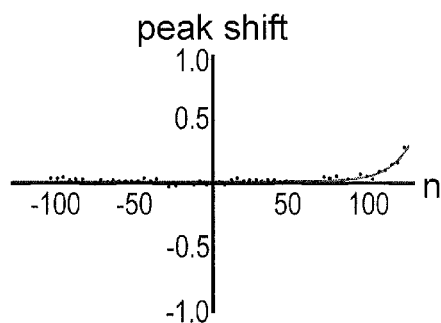
FIG. 10D is a graph of calculated peak shift amounts according to an embodiment of the present invention.

As shown in FIG. 10A, the echoes measured with the readout pulse 306 of positive polarity show shifts corresponding to about −7 sample points in the readout direction immediately after the rise (n=around −128). Further, as shown in FIG. 10B, the echoes measured with the readout pulse 306 of negative polarity similarly show shifts corresponding to about 7 sample points in the readout direction immediately after the rise (n=around 128). Further, as shown in FIGS. 10C and 10D, it can be seen that shifts are also observed in the phase encoding direction, although the degrees thereof are smaller than those in the readout direction.

Then, the waveform calculation part 234 calculates the waveform of the readout pulse 306 (Step S1109). The waveform calculation part 234 obtains time change (waveform) of the gradient magnetic field amplitude Or of the readout pulse 306 by differentiating the shift amounts. This is because the shift amount of the echo peak is determined by time integral value (application amount) of the gradient magnetic field of the readout pulse 306.

Specifically, the waveform calculation part 234 of this embodiment calculates waveform Gr(m) of the gradient magnetic field amplitude Gr of the readout pulse 306 by using the shift amount hcr(n) calculated by the shift amount calculation part 232 in accordance with the following equation (5).

$$Gr(m)=d/dm(f^{-1}(m)) \quad (m=-128,\ldots,127) \quad (5)$$

In the equation, d/dm means differentiation with m, m represents sampling point, and m=f(n)=hcr(n)+n.

Figure 11A:
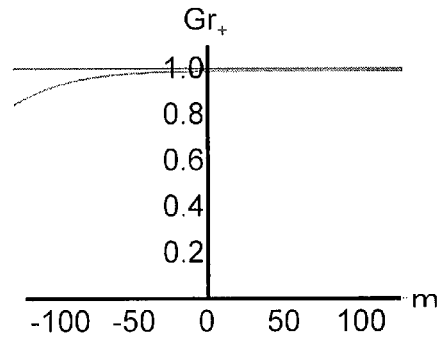
FIG. 11A is an explanatory drawing for explaining waveform of the gradient magnetic field of the calculated readout pulse according to an embodiment of the present invention.
Figure 11B:
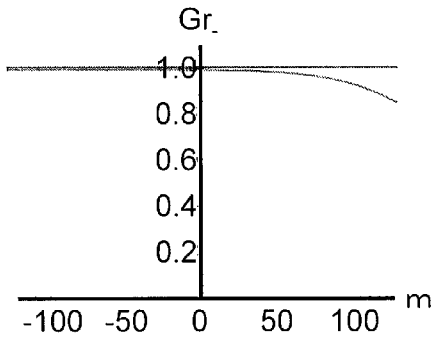
FIG. 11B is an explanatory drawing for explaining waveform of the gradient magnetic field of the calculated readout pulse according to an embodiment of the present invention.

The waveforms of the gradient magnetic field obtained in the example of the measurement are shown in FIG. 11. FIG. 11A shows waveform of the gradient magnetic field obtained from k-space data obtained with the readout pulse 306 of positive polarity, and FIG. 11B shows waveform of the gradient magnetic field obtained from k-space data obtained with the readout pulse 306 of negative polarity. The amplitude of the readout pulse 306 used above was set to be 1.

As is shown in this figure, in the example of the measurement, 15% of under shoots were observed with both the positive and negative polarities of the readout pulse 306, and time constant giving a value close to the set value was 190 μs.

Then, the distortion amount calculation part 233 calculates the distortion amount of the k-space (Step S1110). The distortion amount calculation part 233 calculates distortion of the k-space by using the shift amounts hcr(n) and hcp(n) in both the directions calculated by the shift amount calculation part 232. From the shift amount calculated from the k-space data obtained with the positive polarity and the shift amount calculated from the k-space data obtained with the negative polarity, distortion amounts are independently calculated.

The distortion amount calculation part 233 calculates a point kr(m) on the k-space to be actually sampled as the distortion amount in the kr direction. kr(m) is calculated in accordance with the following equation (6).

$$kr(m)=f^{-1}(m) \quad (6)$$

Further, the distortion amount calculation part 233 calculates a shift Δkp (m) of the k-space in the kp direction as the distortion amount in the kp direction. Δkp(m) is calculated in accordance with the following equation (7).

$$\Delta kp(m)=hcp(kr(m)) \quad (7)$$

In addition, it is also possible to calculate waveform of eddy current generated in the phase encoding direction during the echo measurement by differentiating Δkp(m) for m.

According to the aforementioned procedures, the correction information calculation part 221 of this embodiment calculates correction information. Either the waveform calculation processing to be performed by the waveform calculation part 234 or the distortion amount calculation processing to be performed by the distortion amount calculation part 233 may be performed first. Further, only one of them may be performed.

The calculated correction information is stored in the storage medium 111 or the like. Then, in the following main scan, the correction part 222 calculates values on the k-space grid by gridding from the echoes obtained by the measurement part 210 using kr(m) and Δkp (m) calculated by the distortion amount calculation part 233. In this calculation, the values on the k-space grid are calculated by using the distortion amount calculated from the k-space data obtained by applying a readout gradient magnetic field pulse of the same polarity as that of the readout gradient magnetic field pulse used for the main scan. Data free from k-space distortion are thereby obtained in the main scan.

Then, the image reconstruction part 223 performs conversion processing such as the half Fourier transform for the data not containing k-space distortion, i.e., the values on the k-space grid obtained by the correction part 222, to reconstruct an image.

Figure 12:
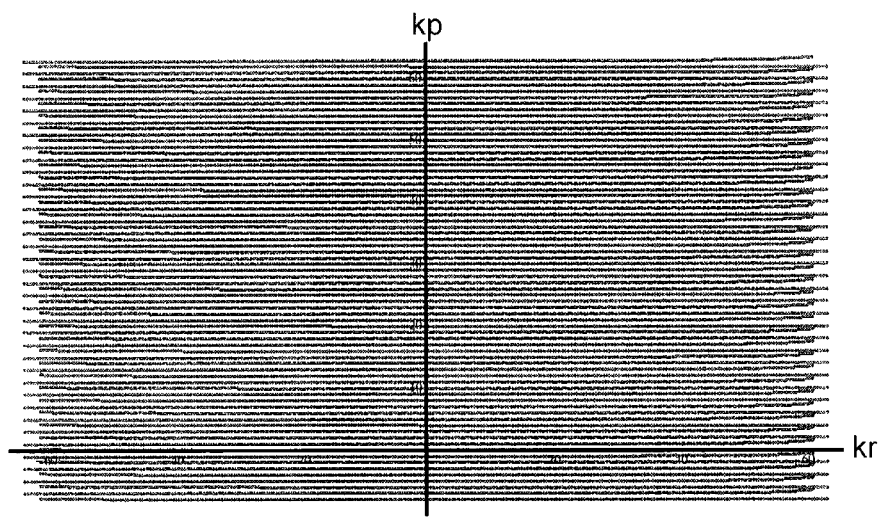
FIG. 12 is an explanatory drawing for explaining the k-space data obtained by the main scan according to an embodiment of the present invention.

Hereafter, effect of the correction performed by the correction information calculation part 221 and the correction part 222 of this embodiment will be described. First, the k-space in which echoes obtained by the main scan are arranged is shown in FIG. 12. These are results obtained by the main scan performed with the same measurement conditions as those of the aforementioned example of the measurement.

As shown in this figure, it can be seen that the k-space is significantly contracted to right and left in the readout direction (kr) for which the waveform is significantly distorted. Degrees of the contraction are inversed on the right and left for every echo. At the both ends, the larger contraction value was 6.0, and the smaller contraction value was 1.1. Further, the maximum shift in the phase encoding direction observed with positive gradient magnetic field was 0.22, and the same observed with negative gradient magnetic field was 0.31.

The images reconstructed by using these k-space data are shown in FIG. 13. The image 510 shown in FIG. 13A is an image reconstructed from the data as they are without performing the correction of this embodiment, and the image 520 shown in FIG. 13B is an image reconstructed from the data subjected to the correction of this embodiment, i.e., an image reconstructed from the data on the grid obtained by gridding using the distortion amounts of the k-space. Contrast emphasized images 511 and 521 are shown on the right sides of them, respectively.

In the images shown in FIG. 13A, N/2 ghosts are clearly observed at the positions indicated with arrows. On the other hand, in the images shown in FIG. 13B, N/2 ghosts are substantially suppressed.

On the basis of the above results, it could be confirmed that the results of the measurement of the gradient magnetic field waveform performed by the distortion amount calculation part of this embodiment were reasonable.

As explained above, according to this embodiment, two-dimensional data are used for obtaining distortion of the k-space caused by distortion of the gradient magnetic field pulse waveform, and therefore time shifts of echoes can be obtained in two directions of the readout direction and the phase encoding direction.

Therefore, according to this embodiment, distortion of the k-space can be calculated and corrected not only in the readout direction but also in the phase encoding direction by using the obtained echo shifts in the two directions. Therefore, there can be obtained an image of high quality with less ghosts compared an image obtained by correcting the distortion only in the readout direction. In particular, in high-speed imaging techniques in which measurement of echoes is started during or immediately after rise of the readout gradient magnetic field pulse, high effect can be obtained.

Further, according to this embodiment, waveform of the readout gradient magnetic field pulse and waveform of the eddy current in the phase encoding direction are calculated by using the obtained echo shifts in the two directions. That is, not only the waveform of the readout gradient magnetic field pulse, but also the waveform of the eddy current generated in the phase encoding direction can be correctly calculated without using any additional measurement apparatus. Therefore, by adjusting the waveform of the readout gradient magnetic field pulse to be applied in the main scan and the waveform of the eddy current in the phase encoding direction beforehand through hardware or software with reference to the above calculation results, degradation of image quality due to waveform distortion can be suppressed. The adjustment is performed by, for example, a method of adjusting output value of power supply so that the readout waveform returns to the designed waveform with reference to the obtained waveform distortion, or amplitude of the eddy current waveform in the phase encoding direction becomes zero, or the like. In such a case, the distortion amount calculation part 233 and the correction part 222 may not be provided. Alternatively, when it is difficult to perfectly adjust the waveform of the readout gradient magnetic field pulse and the waveform of eddy current in the phase encoding direction, both the distortion amount calculation and the correction may be performed.

Further, the shift amount of the echo peak calculated by the shift amount calculation part 232 may be used for fine adjustment of the waveform of the readout gradient magnetic field pulse used for the main scan and the waveform of eddy current in the phase encoding direction. In this case, the reference measurement is performed whenever the waveform is finely adjusted, and the shift amount of the echo peak calculated by the shift amount calculation part 232 is displayed on the display 110. The operator finely adjusts the waveform so that the displayed shift amount becomes 0. In this case, the MRI apparatus 100 is further provided with a reception part in receiving directions of waveform adjustment from the operator. Alternatively, the calculated shift amount may be fed back to a waveform adjustment mechanism, and the execution of the reference measurement and the calculation of the shift amount may be repeated whenever the waveform is finely adjusted, until the shift amount becomes 0. In this case, for example, the distortion amount calculation part 233, the waveform calculation part 234, and the correction part 222 may not be provided.

In the aforementioned embodiment, the processing part 220 is provided in the computer 109 of the MRI apparatus 100. However, the present invention is not limited to such a configuration. For example, the processing part 220 may be constructed in an information processor independent from the MRI apparatus 100, which can transmit and receive data to or from the computer 109.

Further, the aforementioned embodiment is explained for an example in which the pulse sequence used for the main scan is a sequence for the EPI method. However, the present invention is not limited to such a configuration. For example, the sequence may be a BASG sequence. Also in such a case, correction information (shift amount of echo peak, waveform calculation, k-space distortion) is calculated from results obtained by changing the application amount of the dephase gradient magnetic field pulse, basically as the case of using an EPI sequence (DWEPI sequence).

Figure 14A:
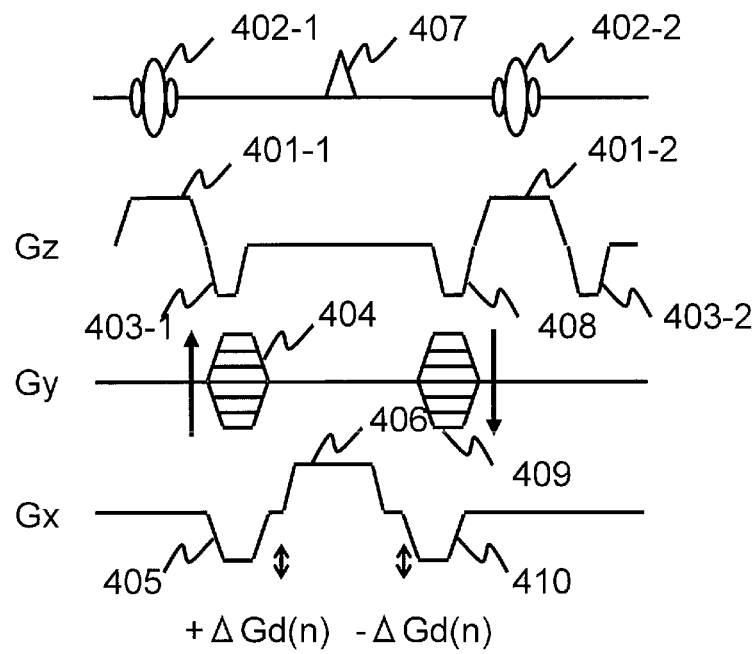
FIG. 14A is an explanatory drawing for explaining a BASG sequence.

An imaging sequence 400 for the BASG method (BASG sequence) is shown in FIG. 14A.

With the BASG sequence 400, a radio frequency magnetic field (RF) pulse 402 is first irradiated together with application of a slice gradient magnetic field pulse 401 in the z-direction to excite magnetization in a certain slice of a subject. Then, after a slice rephase gradient magnetic field pulse 403, a phase encoding gradient magnetic field pulse 404 for giving positional information in the phase encoding direction (y-direction) to the phases of magnetization, and a readout gradient magnetic field pulse 405 for dephase (dephase pulse) are applied, a magnetic resonance signal (echo) 407 is measured with applying a readout gradient magnetic field pulse (readout pulse) 406 for giving positional information in the readout direction (x). Then, in order to make the time integral value of the gradient magnetic field for each axis zero, the gradient magnetic field pulses 408, 409, and 410 are applied for the axes, respectively.

Figure 14B:
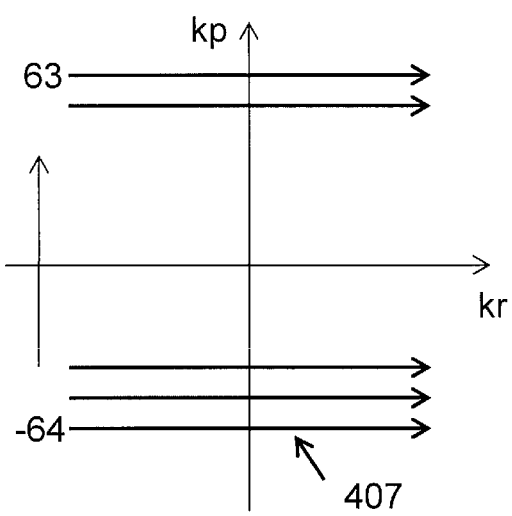
FIG. 14B is an explanatory drawing for explaining the k-space in which echoes obtained with the BASG sequence are arranged.

The aforementioned procedure is repeated with a repetition time TR with changing intensities of the phase encoding gradient magnetic field pulses 404 and 409 (phase encoding amount kp) to measure echoes 407 required for obtain one image. The echoes 407 are arranged on the k-space as shown in FIG. 14B, and an image is reconstructed by two-dimensional inverse Fourier transform.

In the case of using the BASG sequence 400, the polarity of the readout pulse 406 is fixed (a case where the polarity is positive is exemplified in FIG. 14A), unlike the case of using the DWEPI (EPI) sequence 300. Therefore, the direction of the echoes in the readout direction on the k-space is fixed. This pulse sequence provides contrast-reflecting T2 (transverse relaxation time)/T1 (longitudinal relaxation time), thus good contrast between tissue and blood, and therefore it is suitable for morphological and functional diagnoses of the heart, or morphological diagnosis of the abdominal part.

Also when the sequence used in the main scan is the BASG sequence 400, the reference measurement part 231 repeats the unit measurement with changing the application amount (amplitude) of the dephase pulse 405 applied in the readout direction by $\Delta Gd(n)$ as shown in FIG. 14A, as in the case of using the DWEPI (EPI) sequence 300.

However, in the case of using the BASG sequence 400, it is necessary to make the time integral value of the gradient magnetic field zero for every repetition of the pulse sequence with an interval of TR. Therefore, the application amount (amplitude) of the pulse 410 is also changed by $-\Delta Gd(n)$.

The shift amount calculation part 232 calculates shift amounts from a plurality of the obtained k-space data by the same procedure as mentioned above. However, in the BASG sequence 400, the polarity of the readout pulse 406 does not change, and therefore it is not necessary to perform the processing for k-space data separated according to the positive and negative polarities of the readout pulse 406, as performed in the case of using the DWEPI (EPI) sequence 300.

The waveform calculation part 234 and the distortion amount calculation part 233 calculate the waveform and the amount of distortion, respectively, by using the shift amounts calculated by the shift amount calculation part 232 in the same manner as that used in the case of using the DWEPI (EPI) sequence 300.

The aforementioned embodiment is explained by exemplifying a case where the correction information calculation part 221 calculates correction information by using the pulse sequence used for the main scan. However, the present invention is not limited to such a configuration. The k-space distortion induced by the BASG sequence 400 and the k-space distortion induced by the EPI sequence 300 for the data obtained with the same polarity are not usually substantially different from each other. Further, the DWEPI sequence also provides similar results when the eddy current component of long time constant is small, or amplitude of the MPG pulse is made zero. Therefore, for example, it is also possible to correct the k-space distortion measured with one of the BASG sequence 400 and the DWEPI (EPI) sequence 300 by using k-space distortion amount calculated with the other sequence.

In such a case, the DWEPI (EPI) sequence 300 generally enables imaging in a shorter time compared with the BASG sequence 400, and therefore measurement for calculating the k-space distortion using the DWEPI (EPI) sequence 300 can be performed in a shorter time. On the other hand, the BASG sequence 400 generally provides higher SN ratio, and therefore when sufficient SN ratio cannot be obtained with the data obtained with the DWEPI (EPI) sequence 300, the BASG sequence 400 is used.

Since positive and negative waveform distortions are generally substantially the same except for the signs, when the data obtained with the DWEPI (EPI) sequence 300 are corrected by using the data obtained with the BASG sequence 400, distortion of readout pulse of which polarity is different from that of the readout pulse of the BASG sequence 400 can be approximately obtained by reversing the distortion of the readout pulse of the same polarity of the BASG sequence 400.

Further, in the aforementioned embodiment, the correction is performed by using the k-space distortion obtained with the same readout pulse amplitude as that of the imaging sequence for the main scan. However, the present invention is not limited to such a configuration. For example, when the k-space distortion is proportional to the amplitude of the readout pulse, k-space distortion calculated with an imaging sequence of a different readout pulse amplitude can be used. That is, by multiplying the k-space distortion calculated through correction information calculation processing with (readout pulse amplitude for the main scan)/(readout pulse amplitude for the correction information calculation), the k-space distortion given by the imaging sequence for the main scan can be obtained.

As explained above, the MRI apparatus of this embodiment comprises a signal measurement part (measurement part 210) for applying a radio frequency magnetic field and a gradient magnetic field to a subject placed in a static magnetic field and measuring magnetic resonance signals generated from the subject, and a processor (processing part 220) for controlling the signal measurement part and processing the magnetic resonance signals measured by the signal measurement part, and is characterized in that the processor comprises a correction information calculator (correction information calculation part 221) for calculating correction information used for eliminating distortion of the measured magnetic resonance signals, and the correction information calculator comprises a reference measurement part (reference measurement part 231) for controlling the signal measurement part to repeat a unit measurement consisting of applying a readout gradient magnetic field and a phase encoding gradient magnetic field with changing phase encoding amount to repeatedly obtain echoes, and arranging a plurality of the obtained echoes in the k-space to obtain one set of k-space data with changing dephase readout amount to obtain a plurality of sets of k-space data, and a shift amount calculator (shift amount calculation part 232) for calculating shift amounts of peak positions of the echoes in the application direction of the readout gradient magnetic field and the application direction of the phase encoding gradient magnetic field from the plurality of sets of the k-space data, and the correction information calculator calculates the correction information by using the calculated shift amounts.

The correction information calculator may further comprise a distortion amount calculator (distortion amount calculation part 233) for calculating distortion amounts of the k-space in the application direction of the readout gradient magnetic field and the application direction of the phase encoding gradient magnetic field by using the shift amounts. Further, the processor may further comprise a correction part (correction part 222) for calculating values on the k-space grid from main scan k-space data obtained in the main scan using the distortion amounts in both the directions calculated by the distortion amount calculator, and an image reconstruction part (image reconstruction part 223) for reconstructing an image by using the values on the k-space grid calculated by the correction part. Further, the same pulse sequence as the pulse sequence used for the unit measurement may be used for the main scan. Furthermore, the correction information calculator may further comprise a waveform calculator (waveform calculation part 234) for calculating waveform of the readout gradient magnetic field as the correction information by differentiating the shift amounts.

Further, a waveform adjustor for adjusting the waveform of the readout gradient magnetic field on the basis of the waveform calculated by the waveform calculator may be further provided. Further, there may be further provided a display part (display part 230) for displaying the results obtained by the processor, and a waveform adjustment direction receiver for receiving directions for adjustment of waveform, and the display part may display shift amount obtained as a result of the waveform adjustment received through the waveform adjustment direction receiver or shift amount calculated by the shift amount calculator.

Further, the reference measurement part may change the dephase readout amount by changing amplitude of the gradient magnetic applied as a dephase readout gradient magnetic field. Further, the reference measurement part may change the dephase readout amount by a fixed change amount for every unit measurement. In such a case, the change amount may be such an amount that echo peak shifts by a predetermined number of sample points when the readout gradient magnetic field pulse has an ideal waveform. Further, in such a case, the shift amount calculator may comprise an echo moving part for moving each of the plurality of sets of k-space data by a number of sample points by which the echo peak shifts in a direction opposite to the readout direction, a phase image creator for reconstructing a phase image from each of the plurality of sets of moved k-space data, and a linear component calculator for calculating linear components of phase changes corresponding to the change amounts in the readout direction and the phase encoding direction from a plurality of the created phase images, and the shift amount calculator may calculate the shift amounts by using the linear components.

Further, the reference measurement part may alternately change the polarity of the readout gradient magnetic field pulse applied for obtaining the echoes between positive and negative polarities for every application, the shift amount calculator may calculate independent shift amounts from the k-space data obtained by applying the readout gradient magnetic field pulse of positive polarity and the k-space data obtained by applying the readout gradient magnetic field pulse of negative polarity, and the distortion amount calculator may calculate independent distortion amounts from the shift amounts, respectively. Further, the correction part may calculate the values on the k-space grid by using the distortion amounts calculated from the k-space data obtained by applying the readout gradient magnetic field pulse of the same polarity as that of the readout gradient magnetic field pulse used for the main scan. Further, the correction part may calculate the values on the k-space grid using distortion amounts obtained by converting the distortion amounts in proportion to the amplitude of the readout pulse for the main scan. Further, the change amount of the dephase readout amount may be from 0 to ½ of the application amount of the readout gradient magnetic field pulse.

EXPLANATION OF REFERENCES

100: MRI apparatus, 101: magnet, 102: gradient coil, 103: subject, 104: sequencer, 105: gradient magnetic field power supply, 106: radio frequency magnetic field generator, 107: probe, 108: receiver, 109: computer, 110: display, 111: storage medium, 210: measurement part, 220: processing part, 221: correction information calculation part, 222: correction part, 223: image reconstruction part, 230: display part, 231: reference measurement part, 232: shift amount calculation part, 233: distortion amount calculation part, 234: waveform calculation part, 300: DWEPI sequence, 301: slice gradient magnetic field pulse, 302: RF pulse, 303: slice rephase gradient magnetic field pulse, 304: phase encoding gradient magnetic field pulse for dephase, 305: dephase pulse, 306: readout pulse, 307: echo, 309: 180° pulse, 310: phase encoding pulse, 311: MPG pulse, 312: MPG pulse, 401: slice gradient magnetic field pulse, 402: RF pulse, 403: slice rephase gradient magnetic field pulse, 404: phase encoding gradient magnetic field pulse, 405: dephase pulse, 406: readout pulse, 407: echo, 408: gradient magnetic field pulse, 409: gradient magnetic field pulse, 410: gradient magnetic field pulse, 510: image, 511: image, 520: image, 521: image

The invention claimed is:

1. A magnetic resonance imaging apparatus comprising a signal measurement part for applying a radio frequency magnetic field and a gradient magnetic field to a subject placed in a static magnetic field and measuring magnetic resonance signals generated from the subject, and a processor for controlling the signal measurement part and processing the magnetic resonance signals measured by the signal measurement part, wherein, the processor comprises a correction information calculator for calculating correction information used for eliminating distortion of the measured magnetic resonance signals, and the correction information calculator comprises:

a reference measurement part for controlling the signal measurement part to repeat a unit measurement of applying a readout gradient magnetic field and a phase encoding gradient magnetic field with changing phase encoding amount to repeatedly obtain echoes, and arranging a plurality of the obtained echoes in the k-space to obtain one set of k-space data with changing dephase readout amount to obtain a plurality of sets of k-space data, and a shift amount calculator for calculating shift amounts of peak positions of the echoes in the application direction of the readout gradient magnetic field and the application direction of the phase encoding gradient magnetic field from the plurality of sets of the k-space data, and the correction information calculator calculates the correction information by using the calculated shift amounts.

2. The magnetic resonance imaging apparatus according to claim 1, wherein:

the correction information calculator further comprises a distortion amount calculator for calculating distortion amounts of the k-space in the application direction of the readout gradient magnetic field and the application direction of the phase encoding gradient magnetic field as the correction information by using the shift amounts.

3. The magnetic resonance imaging apparatus according to claim 2, wherein:

the processor further comprises:

a correction part for calculating values on the k-space grid from main scan k-space data obtained by the main scan using the distortion amounts in both the directions calculated by the distortion amount calculator, and an image reconstruction part for reconstructing an image by using the values on the k-space grid calculated by the correction part.

4. The magnetic resonance imaging apparatus according to claim 3, wherein:

the reference measurement part alternately changes the polarity of the readout gradient magnetic field pulse applied for obtaining the echoes between positive and negative polarities for every application, the shift amount calculator calculates independent shift amounts from the k-space data obtained by applying the readout gradient magnetic field pulse of positive polarity and the k-space data obtained by applying the readout gradient magnetic field pulse of negative polarity, and the distortion amount calculator calculates independent distortion amounts from the shift amounts.

5. The magnetic resonance imaging apparatus according to claim 4, wherein:

the correction part calculates the values on the k-space grid by using the distortion amounts calculated from the k-space data obtained by applying the readout gradient magnetic field pulse of the same polarity as that of the readout gradient magnetic field pulse used for the main scan.

6. The magnetic resonance imaging apparatus according to claim 3, wherein:

the correction part calculates the values on the k-space grid by using distortion amounts obtained by converting the distortion amounts in proportion to the amplitude of the readout pulse for the main scan.

7. The magnetic resonance imaging apparatus according to claim 2, wherein:

the same pulse sequence as the pulse sequence used for the unit measurement is used for the main scan.

8. The magnetic resonance imaging apparatus according to claim 1, wherein:

the correction information calculator further comprises a waveform calculator for calculating waveform of the readout gradient magnetic field as the correction information by differentiating the shift amounts.

9. The magnetic resonance imaging apparatus according to claim 8 further comprising:

a waveform adjustor for adjusting the waveform of the readout gradient magnetic field on the basis of the waveform calculated by the waveform calculator.

10. The magnetic resonance imaging apparatus according to claim 1 further comprising:

a display part for displaying results obtained by the processor, and a waveform adjustment direction receiver for receiving directions for adjustment of waveform, wherein the display part displays shift amount obtained as a result of the waveform adjustment received through the waveform adjustment direction receiver or shift amount calculated by the shift amount calculator.

11. The magnetic resonance imaging apparatus according to claim 1, wherein:

the reference measurement part changes the dephase readout amount by changing amplitude of the gradient magnetic field applied as a dephase readout gradient magnetic field.

12. The magnetic resonance imaging apparatus according to claim 1, wherein:

the reference measurement part changes the dephase readout amount by a fixed change amount for every unit measurement.

13. The magnetic resonance imaging apparatus according to claim 12, wherein:

the change amount is such an amount that echo peak shifts by a predetermined number of sample points when the readout gradient magnetic field pulse has an ideal waveform.

14. The magnetic resonance imaging apparatus according to claim 13, wherein:

the shift amount calculator comprises:

an echo moving part for moving each of the plurality of sets of k-space data by a number of sample points by which the echo peak shifts in a direction opposite to the readout direction, a phase image creator for reconstructing a phase image from each of the plurality of sets of moved k-space data, and a linear component calculator for calculating linear components of phase changes corresponding to the change amounts in the readout direction and the phase encoding direction from a plurality of the created phase images, and the shift amount calculator calculates the shift amounts by using the linear components.

15. The magnetic resonance imaging apparatus according to claim 1, wherein:

the change amount of the dephase readout amount is from 0 to ½ of the application amount of the readout gradient magnetic field pulse.

* * * * *